United States Patent
Bergaya et al.

(10) Patent No.: US 7,819,663 B2
(45) Date of Patent: Oct. 26, 2010

(54) PREPARATION FOR PRODUCING A MATERIAL USED TO RESTORE A MINERALISED SUBSTANCE, PARTICULARLY IN THE DENTAL FIELD

(75) Inventors: Badreddine Bergaya, Saint-Cyr En Val (FR); Jean-Yves Bottero, Cabries (FR); Marie-Josee Bottero, Cabries (FR); Jean-Claude Franquin, Marseilles (FR); Dominique LeBlanc, Ormesson (FR); Olivier Marie, Soisy sur Seine (FR); Andre Nonat, Epagny (FR); Cyrille Sauvaget, Le Puy Ste Réparade (FR)

(73) Assignee: Septodont Ou Specialties Sertodont S.A., St. Mair des France (FR)

( * ) Notice: Subject to any disclaimer, the term of this patent is extended or adjusted under 35 U.S.C. 154(b) by 388 days.

(21) Appl. No.: 10/524,358

(22) PCT Filed: Aug. 13, 2003

(86) PCT No.: PCT/FR03/02528

§ 371 (c)(1), (2), (4) Date: Aug. 8, 2005

(87) PCT Pub. No.: WO2004/017929

PCT Pub. Date: Mar. 4, 2004

(65) Prior Publication Data

US 2006/0102049 A1 May 18, 2006

(30) Foreign Application Priority Data

Aug. 23, 2002 (FR) ................................ 02 10539

(51) Int. Cl.
- C09K 3/00 (2006.01)
- A61C 5/02 (2006.01)
- A61C 5/04 (2006.01)

(52) U.S. Cl. .................... 433/226; 433/224; 106/35
(58) Field of Classification Search ............... 106/713, 106/724, 35; 433/224, 226
See application file for complete search history.

(56) References Cited

U.S. PATENT DOCUMENTS

| 2,901,377 | A | * | 8/1959 | Bode .......................... 428/413 |
| 5,415,547 | A | | 5/1995 | Torabinejad et al. |
| 5,584,926 | A | * | 12/1996 | Borgholm et al. ........... 106/713 |
| 6,451,105 | B1 | * | 9/2002 | Turpin, Jr. ................... 106/738 |
| 6,858,074 | B2 | * | 2/2005 | Anderson et al. ........... 106/724 |
| 2002/0045678 | A1 | * | 4/2002 | Lopez et al. ................ 523/116 |

FOREIGN PATENT DOCUMENTS

| DE | 199 23 956 A1 | | 11/2000 |
| GB | EP170495 | * | 2/1986 |
| JP | 03165773 | | 7/1991 |
| WO | WO 01/76534 A1 | | 10/2001 |

OTHER PUBLICATIONS

D.P. Bentz et al, Effects of cement particle size distribution on performance properties of portland cement based materials, Cement and Concrete Research vol. 29(10) 1663-1671 1999.*
MSDS Sheet: Calcium Chloride. http://www.jtbaker.com/msds/englishhtml/c0357.htm. Nov. 9, 2007.*
Abdullah. An evaluation of accelerated Portland cement as a resotative material. Biomaterials. vol. 23, Issue 19, Oct. 2002. pp. 4004-4010.*
Schwartz. Mineral Trioxide Aggregate: A new material for endodontics. JADS vol. 130. Jul. 1999. 967-975.*
Article entitled "Mechanism of Effect of Calcium Chloride on Processes of Disperse Strucutre Formation, and Chemical Interaction in Hydration of B-Dicalcium and Tricalcium Silicates", By E.P. Andreeva et al., Colloid J. USSR, vol. 44, No. 4. 1982, pp. 568-573.

* cited by examiner

Primary Examiner—C. Melissa Koslow
Assistant Examiner—Matthew E Hoban
(74) Attorney, Agent, or Firm—Bachman & LaPointe, P.C.

(57) ABSTRACT

A preparation contains an aqueous liquid part, a solid part comprising at least one silicate selected from tricalcium silicate $Ca_2SiO_5$ and dicalcium silicate $Ca_2SiO_4$; and calcium chloride $CaCl_2$ and a water reducing agent which are both contained in at least one of the aforementioned parts. According to the invention, the solid part and the liquid part are intended to be mixed in order to obtain the material. The preparation can be used to restore a mineralized substance, particularly in the dental field.

28 Claims, 1 Drawing Sheet

PREPARATION FOR PRODUCING A MATERIAL USED TO RESTORE A MINERALISED SUBSTANCE, PARTICULARLY IN THE DENTAL FIELD

BACKGROUND OF THE INVENTION (1) Field of the Invention

This invention relates to a preparation for producing a material used to restore a mineralised substance, in particular in the dental field.

(2) Prior Art

In the dental field, the crown is restored so as to overcome, inter alia, the loss of substance associated with the destruction of dental tissue by caries or resulting from a shock.

Until now, the restoration of "impaired" teeth accounts for 75 to 80% of dental treatments (P. Hescot et al.; 1996; Programme International de Recherche de l'Organisation Mondiale de la Santé sur les déterminants et la santébucco-dentaire; Association Dentaire Française).

Currently, dental restoration uses essentially two types of materials for restoration to avoid the need for involvement of a prosthesis laboratory.

The oldest material, used since the 19th Century, is silver amalgam.

Very widely used, its placement by the practitioner is very simple and its mechanical strength has long been demonstrated. Moreover, the average lifespan of an amalgam filling is estimated to be 14 years.

However, silver amalgam has two major disadvantages.

The first disadvantage is associated with the presence of 40 to 50% mercury in its composition. The possible danger of the release of mercury in the saliva and the environment when positioning the material, as well as in wastewater when it is removed, has led to a gradual rejection of the use of this type of material.

The second disadvantage is associated with the inaesthetic metal appearance of fillings made with silver amalgam.

To overcome the disadvantages of the presence of mercury and the inaesthetic appearance of silver amalgams, a second type of restoration material has been developed. It consists of composite resins.

The composite resins are formed by a mixture of organic resin and mineral fillers, which is specifically treated with a product that ensures the binding of the resin to the mineral fillers, without any mercury.

Originally intended for the treatment of anterior teeth, because they satisfy the patients' aesthetic requirements, they are also used for the restoration of posterior teeth.

However, it is noted that the fillings produced with these composite resins have an estimated average lifespan of 7 years, that is half that of the silver amalgam fillings.

This short lifespan of composite resin fillings can be explained by the phenomenon of contraction of the composite resin which occurs during the setting reaction of the composite resins and which no longer provides an adequate marginal seal during the polymerisation reaction, which constitutes a major problem in the use of such resins.

Until now, and in spite of numerous attempts to improve the components of composite resins as well as the associated techniques for use, no composite resin has an adequate marginal seal, in particular in the areas where there is little or no enamel.

In addition, the environmental and aesthetic advantages of composite resins lead to lower spending in terms of public health and savings for the health care budget.

Therefore, there is a real need to have a restoration material for dental reconstitution that offers a compromise between the advantages of silver amalgams, in particular in terms of longevity and mechanical strength, and those of composite resins, namely the absence of mercury and the aesthetic appearance of the filling.

SUMMARY OF THE INVENTION

The objective of this invention is therefore to provide a material used to restore a mineralised substance, in particular for dental restoration, which is capable of resisting pressures of approximately at least 100 Mpa, which moreover has dimensional stability during its placement and after it, and finally has good adhesion to the mineral substance that it is intended to restore.

An additional objective of the invention, in particular in dental applications, is to produce a material having the aforementioned characteristics and which is moreover biocompatible.

Specifically in the dental field, this material must also provide a good marginal seal without any linear contraction so as to ensure an average lifespan approaching that of silver amalgams, provide an aesthetic filling, be resistant to chewing pressures within the pressure value range indicated above, and have a setting time compatible with the handling time necessary for the dental surgeon, i.e. 10 to 30 minutes.

According to the invention, a preparation for producing such a material includes an aqueous liquid part, a solid part containing at least one silicate selected from tricalcium silicate $Ca_3SiO_5$ and dicalcium silicate $Ca_2SiO_4$, calcium chloride $CaCl_2$ and a water-reducing agent, both contained in at least one of the aforementioned parts, in which the solid part and the liquid part are intended to be mixed in order to obtain said material.

Thus, "solid part" refers to all of the solid phases, consisting of the powders of each of its constituents, and "liquid part" refers to the aqueous liquid phase in which the other constituents that make up this liquid part or phase can be added to water.

The water-reducing agent enables the amount of water to be reduced and thus the volume of the liquid phase to be adjusted with respect to that of the solid phase, without adversely affecting the hydration of the tricalcium silicate and/or the dicalcium silicate, which occurs during the mixture of the solid and liquid phases.

The water-reducing agent advantageously has a fluidifying and/or plasticizing capability.

Such properties of the water-reducing agent thus impart fluidity and plasticity on the material obtained after mixture of the preparation according to the invention, making it easier for the practitioner to mix and handle the material.

In particular, plasticizers can be used as water-reducing agents, such as, for example, polynaphthalene sulfonate (PNS) or a plasticizer, referred to as a "superplasticizer", based on modified polycarboxylate.

For dental restoration, the solid part further contains calcium carbonate $CaCO_3$.

Calcium carbonate has an accelerating effect on the hydration of calcium, dicalcium or tricalcium silicate.

Moreover, it enhances the properties of resistance to compression of the material obtained after mixing of the preparation according to the invention.

Preferably, in the dental field, the solid part contains between 70% and 99% by weight of dicalcium and/or tricalcium silicate, and between 1 and 30% by weight of calcium carbonate CaCO₃, these weight percents being given on the basis of all of the constituents of the solid part.

The solid part preferably contains zirconium oxide $Z_rO_2$.

Zirconium oxide has two advantages.

With remarkable hardness, it further enhances the mechanical properties of the material obtained from the preparation according to the invention.

Moreover, by increasing the radio-opacity of this material, the practitioner has improved radiographic control for the restoration of the mineralized substance.

The proportion of zirconium oxide is preferably between 0 and 15% by weight of all of the constituents of this solid part.

According to an embodiment relevant to all of the applications of the present invention, it is the liquid part that contains the $CaCl_2$.

The content of $CaCl_2$ can, for example, be between 1 and 35%, and preferably between 9 and 25%, by weight of the total volume of this liquid part.

In another embodiment, it is the solid part that contains the calcium chloride.

The calcium chloride content in the solid part can, for example, be between 0.1 and 10% by weight of all of the constituents of the solid part, and preferably between 0.9 and 7.5%.

The liquid part can contain the water-reducing agent.

The proportion of water-reducing agent in this liquid part is, for example, between 0.1 and 10% by weight of the total volume of the liquid part, advantageously between 1 and 5% by weight and preferably between 2 and 4%.

In another embodiment, it is the solid part that contains the water-reducing agent.

The content of the water-reducing agent in the solid part is, for example, between 0.01 and 3% by weight of all of the constituents of the solid part, advantageously between 0.15 and 1.25% and preferably between 0.38 and 0.84%.

Plasticizer-type water-reducing agents, such as those mentioned above, can be used in the liquid part or the solid part.

Regardless of the intended uses of the preparations according to the invention, the volume-to-mass ratio between the liquid part and the solid part may be between 0.1 and 0.3, advantageously between 0.15 and 0.25 and preferably between 0.17 and 0.23.

This ratio may vary in particular according to the choice of the water-reducing agent.

In an advantageous embodiment of the invention, the components of the solid part are micronised.

Preferably, an in particular for dental restoration, at least 90% of the particles of each of the constituents of the solid part have a particle size of less than 10 μm.

The invention also relates to a method for making the preparation for producing a material used to restore a mineralised substance, in particular in the dental field, based on the preparation according to the invention.

According to the invention, the solid part and the liquid part are mixed using any means transmitting a high energy to said mixture.

After obtaining a uniform mixture of the two liquid and solid parts, a product with a whitish tint is obtained, which can then be easily implemented.

The material obtained according to the invention, which obviously does not contain mercury, is a more than 95% mineral product, thereby ensuring excellent biocompatibility.

The invention also relates to the use of the preparation according to the invention to obtain a material for restoring teeth, an apical sealing cement, a dentino-cemental substitute, a cavity-lining material and a jawbone filling material.

The preparation according to the invention can specifically be used in the dental field according, inter alia, to the embodiments mentioned as follows, which enable all of the desired characteristics mentioned above to be obtained.

The material according to the invention is particularly promoted for the restoration of teeth, and more specifically, but not limited to posterior teeth, molars and premolars.

It can also be used as an apical sealing cement, by the so-called "retrograde" surgical route or canal route, or as a dentino-cemental substitute in the case of iatrogenic or pathological canal or pulpal floor perforations, but also as a cavity lining with or without pulpal exposure.

The material according to the invention can also be used for filing the bones of the jaw.

Owing to its whitish colour, the dental material is entirely satisfactory with regard to the aesthetic requirement.

It is also entirely possible to consider including a colouring agent in the preparation, in its solid and/or liquid part, so as to increase the range of possible colours.

Thus, it becomes possible to prepare a dental material of which the final colour will perfectly match the colour of the patient's teeth.

BRIEF DESCRIPTION OF THE DRAWINGS

Other properties and advantages of the invention, given as non-limiting examples in reference to the appended figures, are described below.

DETAILED DESCRIPTION OF THE PREFERRED EMBODIMENT(S)

Figure 1:
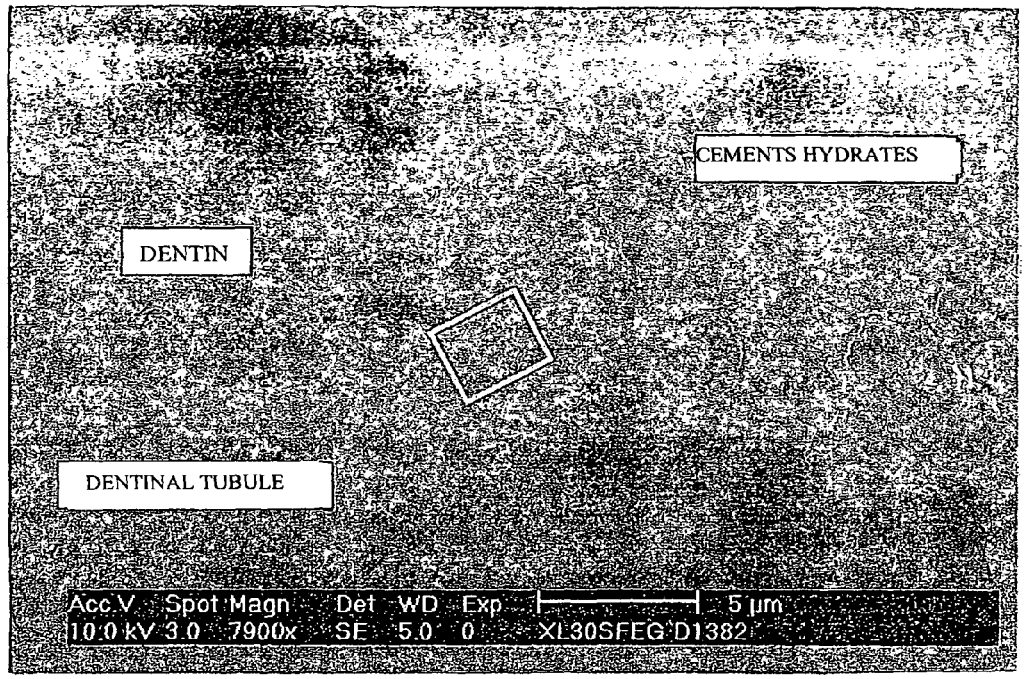
FIG. 1 is a reproduction of an image observed through a scanning electron microscope and showing the polished cross-section of a premolar cavity filled with cement prepared from the preparation according to the invention.

The material according to the invention used as a dental cement to restore the premolar, of which one part is shown in FIG. 1, was prepared from the following preparation, in a liquid part/solid part mass ratio of 0.21:

| Solid part (for 100 g): | |
|---|---|
| $Ca_3SiO_5$ | 85 g |
| $CaCO_3$ | 15 g |
| Liquid part (for 100 ml): | |
| $CaCl_2, 2H_2O$ | 14.7 g |
| water-reducing agent | 3 g |
| water | g.s.f. 100 ml |

The powdered raw materials of the solid part used are micronised at least for this dental use. Preferably and generally, their particle size is less than 10 microns.

In this example, the particle size characteristics of the various constituents are as follows:

| for $Ca_3SiO_5$: | $d_{10} = 0.81$ μm |
|---|---|
| | $d_{50} = 3.16$ μm |
| | $d_{90} = 7.51$ μm | with $d_x$ representing the maximum size reached by x % of the particles of the compound considered, in this case for $Ca_3SiO_5$.

for $CaCO_3$, the average diameter of the particles is between 50 and 100 nm.

According to a different embodiment, the preparation according to the invention can contain zirconium oxide $Z_rO_2$.

Such a preparation can also constitute a dental cement, in particular for apical sealing uses, by the so-called "retrograde" surgical or canal route, for which a material with good radio-opacity is necessary.

Such a cement is prepared from the following preparation:

| Solid part (for 100 g): | |
|---|---|
| $Ca_3SiO_5$ | 80.75 g |
| $CaCO_3$ | 14.25 g |
| $ZrO_2$ | 5.00 g |
| Liquid part (for 100 ml): | |
| $CaCl_2, 2H_2O$ | 14.7 g |
| water-reducing agent | 3 g |
| water | q.s.f. 100 ml | the liquid part/solid part mass ratio in this case is 0.18.

In this second example, the particle size characteristics of $Z_rO_2$ are as follows:

$$d_{10} = 0.28 \mu m$$
$$d_{50} = 0.71 \mu m$$
$$d_{90} = 1.53 \mu m$$

with $d_x$ being defined as above and the particle size characteristics of the two other constituents $Ca_3SiO_5$ and $CaCO_3$ being identical to those of the previous example.

The water-reducing agent used in these two embodiments was a new generation plasticizer, called a "superplasticizer", based on modified polycarboxylate sold by the Chryso company under the trade name "Chrysofluid Premia".

The practitioner extemporaneously mixes the solid and liquid parts then places the dental material obtained, for example with an amalgam carrier, for the dental work to be carried out.

In this case, after mixing one of the preparations discussed in the examples above, the cement was inserted into a premolar cavity, using the conventional tools of the practitioner.

In the aforementioned examples, the preparations discussed were mixed using an automatic mixing means transmitting to the preparations a high energy so as to obtain a uniform paste that can then be placed using an amalgam carrier.

The setting time of the material in the dental application according to the invention is compatible with the handling time of the practitioner, and is obtained without the intervention or addition of any substance: this setting indeed occurs without any photo- or chemically-polymerizable monomer additive and without the use of ultrasound as is the case with the current resins.

Under conditions of use at 100% moisture and 37° Celsius, a dental material is obtained having all of the desired characteristics, such as:

no shrinkage over time, with perfect dimensional stability,
resistance to compression within 24 hours of 100 to 200 Mpa,
good adhesion to the dental tissue as shown in the appended figures,
acceptable aesthetic appearance,
non-solubility after setting,
electrical and thermal insulation,
hardness suitable for chewing, and
simple and practical clinical handling of the preparation, and thus of the material obtained after mixing this preparation.

In FIG. 1, the dentin is identified at the level of its interface with the cavity of the premolar.

This cavity is filled with the material, or dental cement, according to the invention. At the level of the dentin, a dentinal tubule appears, of which one part is indicated with a white box.

Figure 2:
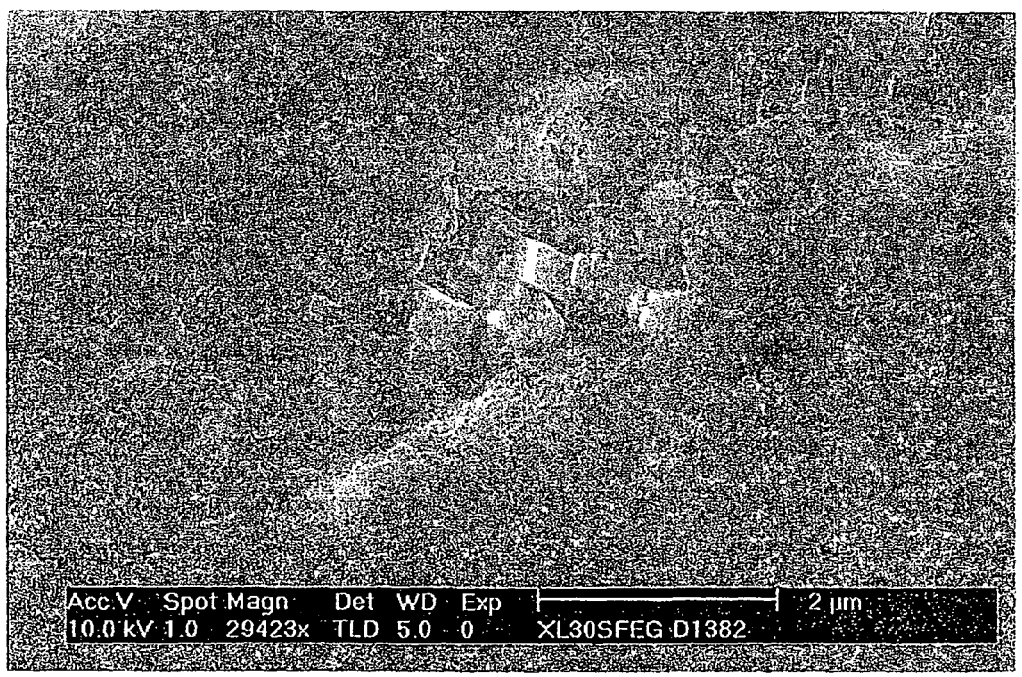
FIG. 2 is an enlarged reproduction of the area indicated with the white box in FIG. 1.

In FIG. 2, the expansion of the box shows in detail the inside of the dentinal tubule. It is noted that this interior is characterized by the presence of a large number of crystals.

An analysis of these crystals has shown that they consist of silicon, which must come from the dental cement inserted into the premolar cavity.

This means that the dental material thus used remarkably fills not only the entire cavity of the tooth, but also that it penetrates the inside of the dentinal tubules passing through the dentin.

Thus, by creating physicochemical bonds with the mineralised tissues, and in particular the dentin, the dental cement enables a good marginal seal to be obtained.

This good marginal seal is reinforced by the fact that the dental cement maintains its dimensional stability: indeed, no linear contraction has been observed.

Moreover, this dental cement has the mechanical properties necessary for a material for filling teeth, in particular posterior teeth, and is probably of a durability greater than composite resins.

Furthermore, the material obtained from the preparation according to the invention is not cytotoxic, and is therefore particularly beneficial.

The evaluation of cytotoxicity, and therefore the possible toxic activity of the cement on certain cells leading to their destruction, has been conducted according to the AFNOR protocol, standard S 99-505-5, NF EN, ISO 10 993-5 of December 1999.

The cellular mortality rate observed at three different times—3 hours, 1 day and 7 days, respectively, after the setting of the cement, was in all three cases lower than 10%, which corresponds to zero toxicity according to this AFNOR standard.

Although this describes more specifically a preparation for dental restoration, it relates more generally to a material for restoring a mineralised substance, without any restriction on the scope of the invention.

Such a material can thus be used as an apical sealing material, by the so-called "retrograde" surgical or canal route, as a dental cement substitute, in the case of iatrogenic or pathological canal or pulpal floor perforations, as a cavity lining with or without pulpal exposure, or as a filling material for jaw bones.

The invention claimed is:

1. A process for producing a material for restoring a mineralized substance in the dental field and for restoring said mineralized substance, said process comprising the steps of:
   providing an aqueous liquid part;
   providing a solid part consisting of between 1 and 30% by weight of calcium carbonate and between 70% and 99% by weight of at least one silicate selected from tricalcium silicate and dicalcium silicate, optionally an amount of a radio-opacity increasing agent, and optionally an amount of a colouring agent;

providing calcium chloride and a water-reducing agent, both contained in the aqueous liquid part;

obtaining a uniform mixture of the solid part and the liquid part; and restoring said mineralized substance by using said uniform mixture as an apical sealing cement, by retrograde surgical route or canal route, or as a dentino-cemental substitute in the case of iatrogenic or pathological canal or pulpal floor perforations, or as a cavity-lining material with or without pulpal exposure, or a jawbone filling material, by placing said uniform mixture on a tooth part to be restored and allowing the mixture placed on the tooth part to set.

2. A process according to claim 1, wherein the solid part and the liquid part are mixed using means for transmitting a high energy to said mixture in order to obtain a uniform paste.

3. A process according to claim 1, wherein the tooth-restoration material is used with an amalgam carrier.

4. A process according to claim 1, wherein the mixture is used for the restoration of posterior teeth.

5. A process according to claim 1, wherein the mixture has a setting time which is compatible with a handling time by a practitioner in the dental field.

6. A process according to claim 1, wherein the radio-opacity increasing agent is zirconium oxide and said zirconium oxide is present in an amount up to 15% by weight of all the constituents of the solid part.

7. A process according to claim 1, wherein the liquid part contains calcium chloride dihydrate ($CaCl_2$, $2H_2O$) with a content between 1 and 35% by weight with respect to a total volume of the liquid part.

8. A process according to claim 7, wherein said calcium chloride dihydrate ($CaCl_2$, $2H_2O$) is present in a content between 9 and 25% by weight with respect to the total volume of the liquid part.

9. A process according to claim 1, wherein the liquid part contains a water-reducing agent in a proportion between 0.1 and 10% by weight of a total volume of the liquid part.

10. A process according to claim 9, wherein said water-reducing agent is present in an amount from 1.0 to 5.0% by weight of the total volume of the liquid part.

11. A process according to claim 9, wherein said water-reducing agent is present in an amount from 2.0 to 4.0% by weight of the total volume of the liquid part.

12. A process according to claim 9, wherein the water reducing agent is a plasticizer.

13. A process according to claim 12, wherein the water-reducing agent is selected from the group consisting of polynaphthalene sulfonate and a modified polycarboxylate-based plasticizer.

14. A process according to claim 1, wherein the liquid part/solid part mass ratio is between 0.1 and 0.3.

15. A process according to claim 14, wherein the liquid part/solid part mass ratio is between 0.15 and 0.25.

16. A process according to claim 14, wherein the liquid part/solid part mass ratio is between 0.17 and 0.23.

17. A process according to claim 1, wherein at least 90% of the particles of each of the constituents of the solid part has a particle size of less than 10 µm.

18. A process according to claim 1, wherein the solid part further includes a radio-opacity increasing agent in order to improve radiographic control for restoration of the mineralized substance.

19. A process for producing a material for restoring a mineralized substance in the dental field and for restoring said mineralized substance, said process comprising the steps of:

providing an aqueous liquid part;

providing a solid part consisting of between 1 and 30% by weight of calcium carbonate and between 70% and 99% by weight of at least one silicate selected from tricalcium silicate and dicalcium silicate, calcium chloride dihydrate ($CaCl_2$, $2H_2O$) with a content between 0.1 and 10% by weight of all of constituents of the solid part, optionally an amount of a radio-opacity increasing agent, and optionally an amount of a colouring agent;

obtaining a uniform mixture of the solid part and the liquid part; and restoring said mineralized substance by using said uniform mixture as an apical sealing cement, by retrograde surgical route or canal route, or as a dentino-cemental substitute in the case of iatrogenic or pathological canal or pulpal floor perforations, or as a cavity-lining material with or without pulpal exposure, or a jawbone filling material, by placing said uniform mixture on a tooth part to be restored and allowing the mixture placed on the tooth part to set.

20. A process according to claim 19, wherein said calcium chloride dihydrate ($CaCl_2$, $2H_2O$) is present in an amount between 0.9 and 7.5%.

21. A process for producing a material for restoring a mineralized substance in the dental field and for restoring said mineralized substance, said process comprising the steps of:

providing an aqueous liquid part;

providing a solid part consisting of between 1 and 30% by weight of calcium carbonate and between 70% and 99% by weight of at least one silicate selected from tricalcium silicate and dicalcium silicate, an amount of calcium chloride, optionally an amount of a radio-opacity increasing agent, and optionally an amount of a colouring agent;

providing a water-reducing agent in the aqueous liquid part;

obtaining a uniform mixture of the solid part and the liquid part; and restoring said mineralized substance by using said uniform mixture as an apical sealing cement, by retrograde surgical route or canal route, or as a dentino-cemental substitute in the case of iatrogenic or pathological canal or pulpal floor perforations, or as a cavity-lining material with or without pulpal exposure, or a jawbone filling material, by placing said uniform mixture on a tooth part to be restored and allowing the mixture placed on the tooth part to set.

22. A process for producing a material for restoring a mineralized substance in the dental field and for restoring said mineralized substance, said process comprising the steps of:

providing an aqueous liquid part;

providing a solid part consisting of between 1 and 30% by weight of calcium carbonate and between 70% and 99% by weight of at least one silicate selected from tricalcium silicate and dicalcium silicate, an amount of a water reducing agent, optionally an amount of a radio-opacity increasing agent, and optionally an amount of a colouring agent;

providing calcium chloride in the aqueous liquid part;

obtaining a uniform mixture of the solid part and the liquid part; and restoring said mineralized substance by using said uniform mixture as an apical sealing cement, by retrograde surgical route or canal route, or as a dentino-cemental substitute in the case of iatrogenic or pathological canal or pulpal floor perforations, or as a cavity-lining material with or without pulpal exposure, or a jawbone filling material, by placing said uniform mixture on a tooth part to be restored and allowing the mixture placed on the tooth part to set.

23. A process according to claim 22, wherein the water-reducing agent is present in a proportion between 0.01 and 3% by weight of all of constituents of the solid part.

24. A process according to claim 23, wherein said water-reducing agent is present in an amount from 0.15 to 1.25% by weight of all the constituents of the solid part.

25. A process according to claim 23, wherein said water-reducing agent is present in an amount from 0.38 to 0.84% by weight of all the constituents of the solid part.

26. A process according to claim 23, wherein the water-reducing agent is a plasticizer.

27. A process according to claim 26, wherein the water-reducing agent is selected from the group consisting of polynaphthalene sulfonate and a modified polycarboxylate-based plasticizer.

28. A process for producing a material for restoring a mineralized substance in the dental field and for restoring said mineralized substance, said process comprising the steps of:
 providing an aqueous liquid part;
 providing a solid part consisting of between 1 and 30% by weight of calcium carbonate and between 70% and 99% by weight of at least one silicate selected from tricalcium silicate and dicalcium silicate, an amount of calcium chloride, an amount of a water reducing agent, optionally an amount of a radio-opacity increasing agent, and optionally an amount of a colouring agent;
 obtaining a uniform mixture of the solid part and the liquid part; and
 restoring said mineralized substance by using said uniform mixture as an apical sealing cement, by retrograde surgical route or canal route, or as a dentino-cemental substitute in the case of iatrogenic or pathological canal or pulpal floor perforations, or as a cavity-lining material with or without pulpal exposure, or a jawbone filling material, by placing said uniform mixture on a tooth part to be restored and allowing the mixture placed on the tooth part to set.

* * * * *